United States Patent [19] [11] 3,992,087
Flom et al. [45] Nov. 16, 1976

[54] VISUAL ACUITY TESTER
[75] Inventors: Merton C. Flom; Anthony J. Adams, both of Oakland, Calif.
[73] Assignee: Optical Sciences Group, Inc., San Rafael, Calif.
[22] Filed: Sept. 3, 1975
[21] Appl. No.: 609,962

[52] U.S. Cl. .................................... 351/7; 351/13; 351/30
[51] Int. Cl.² ......................................... A61B 3/14
[58] Field of Search ................. 351/31, 30, 13, 6, 7

[56] References Cited
UNITED STATES PATENTS
3,473,868 10/1969 Young et al. ............................ 351/6
3,679,295 7/1972 Newman ................................. 351/6
3,827,789 8/1974 Molner ................................. 351/30

Primary Examiner—Harold A. Dixon
Attorney, Agent, or Firm—Harris Zimmerman

[57] ABSTRACT

A device for objectively determining visual acuity includes a viewing screen on which a moving spot of light of diminishing intensity is projected. Infrared eye tracking sensors scan the eyes of the subject and generate a voltage analog signal of the eyes' position. The position signal is compared with a signal representing the position of the moving spot, and the difference is fed to a threshold detector circuit. As the spot becomes too dim to be seen by the subject, the eyes fail to track the spot, and the difference between the two signals surpasses the threshold of the detector circuit. The brightness of the spot when last tracked successfully, which correlates with standard visual acuity measurements, is then displayed as the visual acuity of the subject.

9 Claims, 4 Drawing Figures

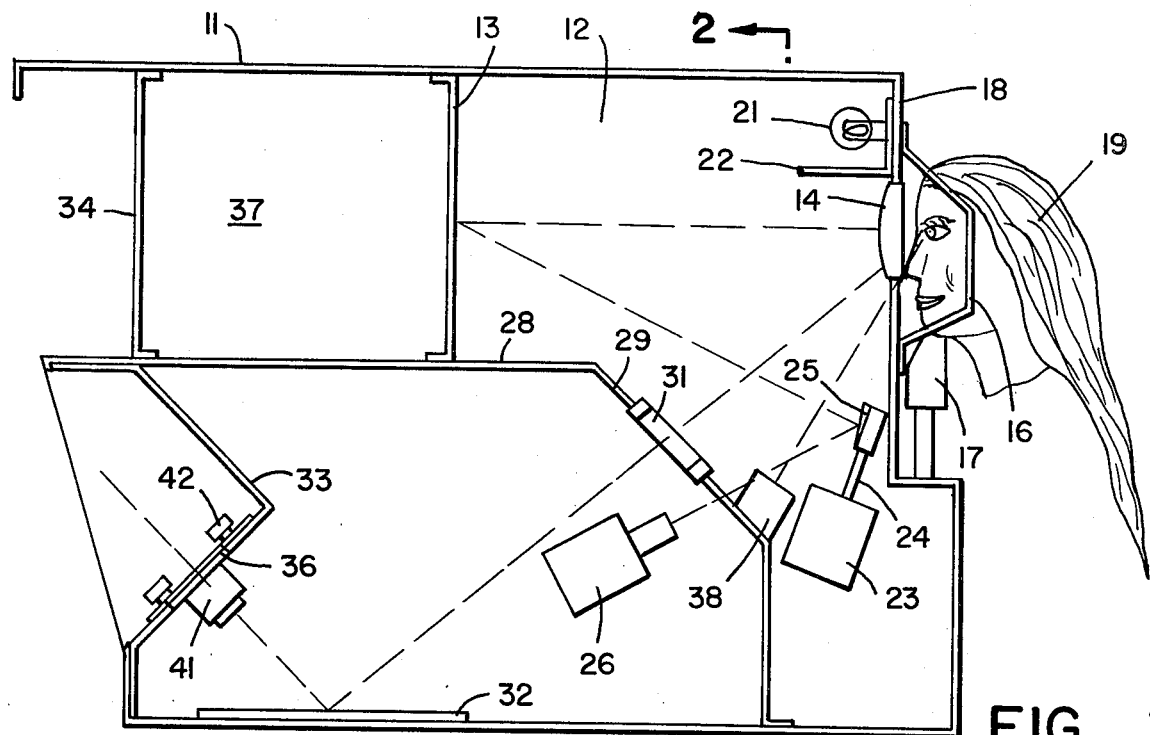
FIG_1
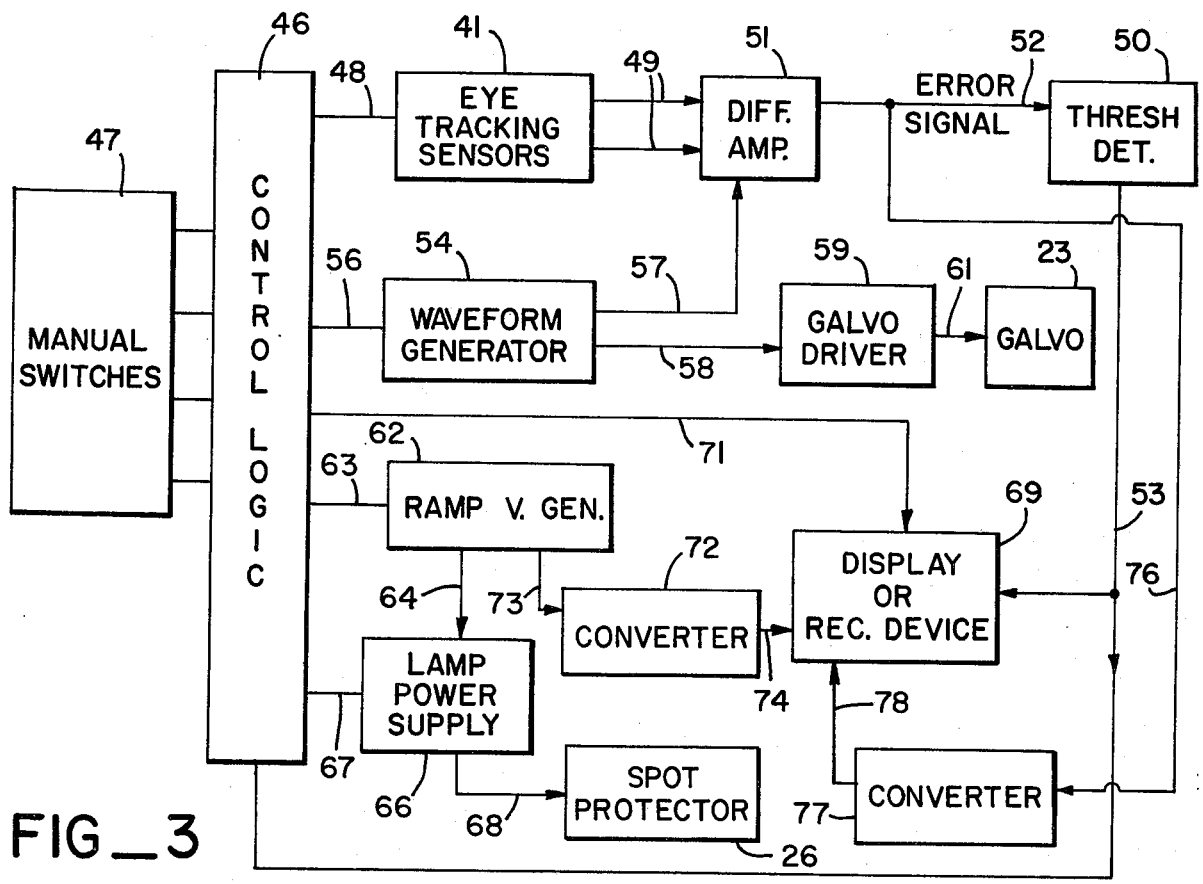
FIG_3

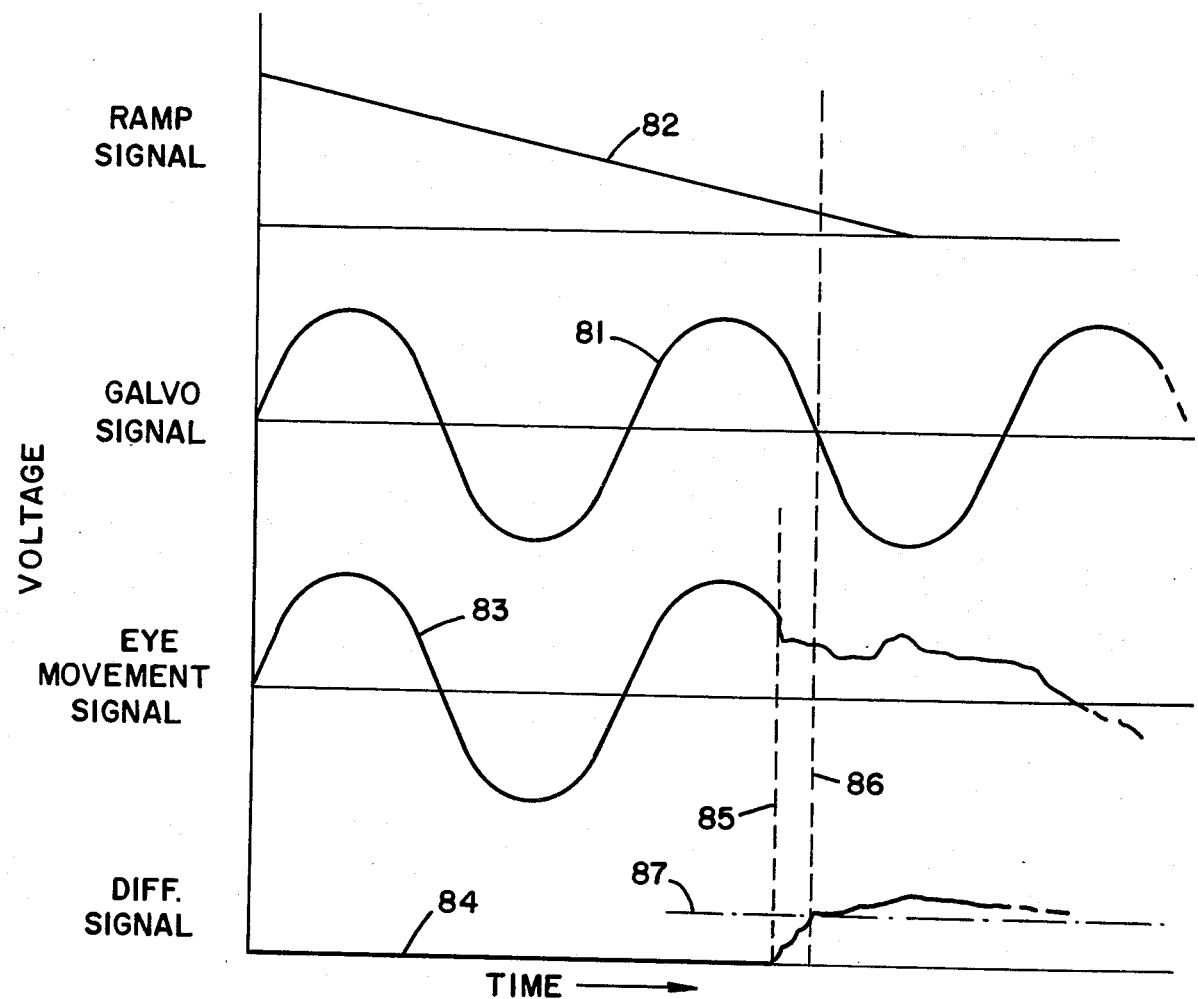
FIG_4
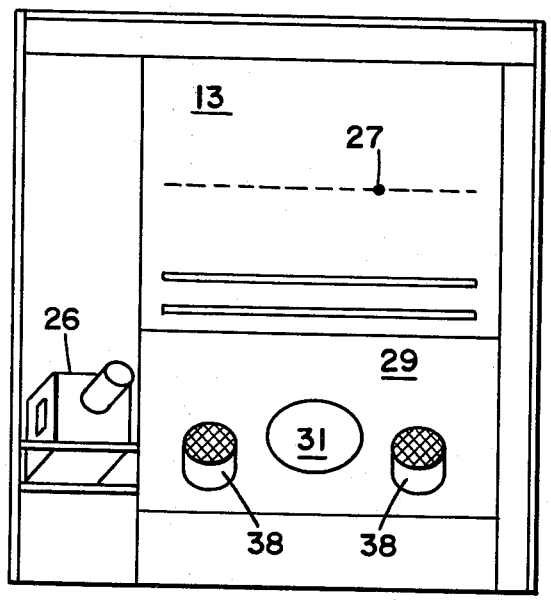
FIG_2

VISUAL ACUITY TESTER

BACKGROUND OF THE INVENTION

Visual acuity is a physiological factor of primary importance in determining qualifications for job placement, licenses, and the like. Most often it is determined through the use of the Snellen letter chart, in which the threshold letter size for the subject is found and converted to a visual acuity measurement. This procedure is subject to several subtle variables which can significantly affect the outcome, such as inappropriate room lighting, test lamp aging, failure of examinee to cover each eye properly, examiner recording error, and inherent testing pressures.

Furthermore, the results of such a visual acuity test are seriously affected by the desires of the subject. For example, in Armed Forces enlistment induction, drivers license testing, or in the case of children who do not wish to wear glasses, an individual with poor acuity may memorize the Snellen chart to achieve a "passing" score. On the other hand, those who wish to avoid Armed Forces draft induction may purposely misread the Snellen chart to score below the minimum acceptable visual acuity level.

Also, it is often difficult to ascertain the visual acuity of children, due to their unfamiliarity with the letters of the Snellen chart, or their unwillingness to cooperate with the examiner in the testing procedure. Failure to diagnose vision problems in children, due to such testing difficulties, may result in unexplained low learning achievement, exacerbated visual abnormalities, and other serious consequences.

SUMMARY OF THE INVENTION

The present invention provides a device for objectively determining the visual acuity of a subject which is not subject to the causes of error found in prior art methods and devices. Generally the invention provides a screen in the field of vision of the subject, on which is projected a small spot of light which is reflected thereto by a mirror carried on a galvanometer. A long-period A.C. signal is fed to the galvanometer, causing the mirror to reflect the spot in scanning fashion over the screen.

The eyes of the subject are illuminated by an infrared light source, and infrared tracking sensors are trained on the eyes to detect any movement. As the spot moves across the screen the eyes follow by voluntary or involuntary response, and the infrared sensors generate an eye movement signal. This eye movement signal is compared to the A.C. galvanometer signal by a differential amplifier. The difference, or error, signal resulting is fed to a threshold detector circuit.

The contrast between the spot and background is reduced by reducing the brightness of the spot. In one embodiment, the brightness of the spot projecting lamp is attenuated by a ramp function generator which powers the lamp. As the brightness of the spot diminishes, the point is reached at which the eyes can no longer follow the spot. They undergo random, or saccadic motion, and the eye tracking sensors produce a signal accordingly. The results in an error signal from the differential amplifier which exceeds the threshold of the detector circuit. Due to the fact that the spot brightness at the instant of eye tracking failure is related directly to visual acuity, the spot brightness can be monitored, directly or indirectly, and the visual acuity displayed through a conversion. In one embodiment the spot brightness is a function of the voltage of the ramp function generator, and the voltage applied to the lamp correlates directly with the visual acuity of the subject. This voltage is fed through a conversion network and displayed in a readout device as visual acuity.

In order to increase the sensitivity of the test or to identify specific diseases when light stress precedes the acuity measure, the spot and background color and luminance may be altered. A simple adjustment of the acuity tester holds contrast fixed and permits variation of the sweep frequency of the spot. Eye movement changes which are produced by drugs such as alcohol are detected by the device when they fail to match the stimulus sweep. For example, the device has been used for the purpose of revealing alcohol intoxication.

The invention is also adapted to measure the phoria of the subject. In this test, polarized light is used to project the spot on the screen, and a pair of polarized filters, each crossed with the other, are placed in the line of sight of the subject so that only one eye sees the spot. The eye tracking sensors are trained on each eye, generating position signals which will diverge if phoria is exhibited. These signals are fed into a differential amplifier, and the resulting difference signal is displayed on a readout device as the phoria of the patient.

THE DRAWING

FIG. 1 is a schematic elevation of the test device of the present invention.

FIG. 2 is a cross-sectional elevation of the test device, taken along line 2—2 of FIG. 1.

FIG. 3 is a block diagram of the electronic circuitry of the present invention.

FIG. 4 is a comparative graph of signal voltages of the test device.

DESCRIPTION OF THE PREFERRED EMBODIMENT

The present invention comprises a device for objectively assessing the visual acuity of a subject. It relies on the newly discovered statistical and physiological fact that the visual acuity of a subject, as measured by standard means, correlates very well with the ability of the subject to see and follow a moving spot of light of diminishing contrast. That is, the dimness of the spot of light at the instant the subject looses sight of it is related directly to standard visual acuity measurement scales, such as the Snell-Sterling percentage.

As shown in FIG. 1, the present invention includes a cabinet 11, in which is disposed a lightproof viewing chamber 12. The chamber includes a vertical viewing screen 13 at one end thereof, and a pair of positive lenses 14 disposed in the wall at the opposite end thereof. A head brace 16 and a chin rest 17 are provided at the exterior end 18 of the cabinet, adapted to support and immobilize the head of a test subject 19. In such a position the subject is able to gaze at the viewing screen without fatigue, the line of sight of each eye directed through one of the respective lenses. The lenses are provided so that the subject views the screen at optical infinity.

Within the viewing chamber is disposed a lamp 21, shielded from the view of the subject by a plate 22. The lamp 21 provides a means of adjustably lighting the viewing screen, and also provides sufficient reflected light through the lenses 14 to illuminate the eyes of the subject. Also disposed within the viewing chamber is a galvanometer 23, from which extends a shaft 24. Joined to the end of the shaft is a mirror 25. A projector 26 may be disposed within the chamber or directed into the chamber, aimed at the mirror 25. The projector is provided with a slide, iris, or the like which permits the projector to project a narrow spot of light 27 (approximately 3 to 5 minutes of arc as seen by the eye) onto the mirror, which is oriented to reflect the spot onto the viewing screen. It may be appreciated that actuation of the galvanometer causes the mirror to rotate about the axis of the shaft, causing the reflected spot to move across the viewing screen through an arc of aproximately 15°.

A console 28 extending into the viewing chamber includes an oblique side 29 which is provided with a viewing port 31 therethrough. Within the console a horizontal mirror 32 is disposed so that the images of the eyes of the subject pass through the port 31 and fall on the mirror 32. A control panel 33 extends obliquely from the end 34 of the cabinet, and is provided with a viewing aperture 36 through which the reflected images of the subject's eyes pass to the examiner. Above the console and adjacent the viewing screen is the electronic circuitry 37 of the invention.

Secured to the console 28 are a pair of infrared light sources 38, directed upwardly through the lenses 14 to illuminate the subject's eyes with infrared radiation. Extending from the control panel are a plurality of infrared eye tracking sensors 41. These sensors are directed obliquely downwardly toward the reflection of the subject's eyes from mirror 32. The position of the sensors is laterally adjustable by means of control knobs 42 on the control panel, so that the exmainer may direct at least a pair of sensors at the image of each eye of the subject.

The electronic circuitry 37 of the present invention, as shown in FIG. 3, includes a control logic system 46 which actuates the other components of the circuitry in accordance with a built-in program. A plurality of manual switches 47, disposed on the control panel (not shown in FIG. 1), permit the examiner to control the functioning of the control logic, and thus of the entire circuit.

Actuation of the eye tracking sensors 41 is controlled by means of line 48 connecting the sensors to the control logic. The signals from the sensors pass through a plurality of conductors 49 to a differential amplifier 51. The output of the differential amplifier is fed through conductor 52 to a threshold detector 50. The threshold detector output is fed through line 53 to a display or recording device 69, and also to the control logic.

A waveform generator 54, which produces an extremely low frequency (approximately 1.0 Hz) signal of sinusoidal or other periodic nature, is actuated through conductor 56 connecting it to the control logic. The output signal from the waveform generator is fed through connection 57 to the differential amplifier, which determines the arithmetic difference between the waveform generator output and the summed signals from the eye tracking sensors. The output signal of the driver 59 is fed through conductor 61 to the galvanometer 23. It should be noted that this device is compatible with any type of device for determining eye position. For example, a simple clip-on infrared eye position (motion) sensor may be clipped on to the subject's spectacles.

A ramp voltage generator 62, which produces a smoothly declining voltage signal, is connected through line 63 to the control logic. The output ramp signal is conducted through line 64 to the lamp power supply 66, which is also connected by line 67 to the control logic. The power supply 66 is connected through line 68 to the spot projector 26. The power supply 66 feed line voltage to the projector with an RMSV value controlled by the amplitude of the ramp signal voltage.

The results of the visual acuity tests are made evident by means of a display or recording device 69, which is connected to the control logic through line 71. The device 69 may comprise a digital readout, a chart recorder, or the like. A signal converter 72, which may comprise a voltage dividing network or a linear amplifier, receives the ramp voltage signal through line 74 to the display device 69. The output signal of the differential amplifier is also fed through line 76 to a converter 77, similar to the converter 72, which produces an output conducted through line 78 to the display device 69.

The functional interrelationships of the various parts of the present invention may best be described by describing the procedure typically used to test visual acuity therewith. First, the subject is placed with his/her head in the brace 16, supported by the chin rest 17. The lamp 21 illuminates the viewing chamber, and, indirectly, through lenses 14, the eyes of the subject. Additional side lights are provided to temporarily illuminate the eyes to facilitate set-up. The infrared light sources 38 are also actuated.

The examiner aligns the infrared sensors 41 with the eyes of the subject, by peering through the viewing aperture 36 and employing the knob controls 42. Each pair of the sensors is aligned with the limbus of the respective eye along the principal horizontal axis thereof. The sensors are then actuated to track the eyes of the subject. The side lights are extinguished, and the waveform generator 54, ramp voltage generator (FIG. 4), amplified by the dirver 59, is presented to the galvanometer 23 which rotates in an oscillating fashion in response thereto. The mirror 25 then causes the spot 27 to horizontally scan the screen 13 with a periodic motion.

At the same time, the ramp voltage signal 82 from the ramp generator 62 is controlling the lamp power supply, so that the intensity of the projected spot is gradually and smoothly diminished. This same effect can be created by use of a variable neutral density filter in the path of the projected spot. The subject watches the scanning spot, his/her eyes being required to move back and forth in an oscillating fashion since the head is immobilized. The eye sensors produce an eye movement signal 83 indicative of this eye motion, i.e., the signal 83 oscillates in correspondence with the galvanometer signal 81, as shown in FIG. 4. The signals 81 and 83 are compared by the differential amplifier 51, producing a difference signal 84 which has substantially zero amplitude as long as the subject is following the spot successfully.

At some point 85 the spot will diminish in contrast to such an extent that the subject, due to his/her visual acuity, will no longer be able to track the spot. At this instant the eyes will cease their oscillating motion and will begin to undergo saccadic motion. The eye movement signal will vary accordingly, the signals 81 and 83 will diverge, and the difference signal 84 will begin to increase in amplitude. Very soon thereafter the difference signal, which is fed to the threshold detector 50, will increase and exceed the threshold level 87 of the detector 50. The threshold detector is thus actuated to produce a signal which is fed to the display device 69 and the control logic.

Upon receiving the signal from the detector, the control logic switches off the waveform generator, ramp generator, and lamp power supply and actuates the display device 69 to display visual acuity units. In this mode, the ramp voltage signal of which the lamp intensity is a function and therefore the visual acuity is a function, is fed through the converter 72 to the display device. The converter may be a linear or non-linear device which has the proper response function to convert the ramp voltage amplitude at the instant 86 to the corresponding, functionally related voltage level which represents the visual acuity of the subject. This value is displayed by device 69 as the visual acuity of the subject, in Snell-Sterling percentage or the like.

This testing procedure, which may require only ten seconds to complete, may be repeated several times within a minute time period. It should be noted that such repetition will yield a more reliable average value for visual acuity. Furthermore, repeated tests prevent willful falsification of test results on the part of the subject. The subject cannot smoothly follow the spot after it has disappeared from view, and so cannot increase his/her acuity result. If the subject is purposely attempting to decrease the visual acuity score, this will quickly become apparent. Since it is impossible for the subject to objectively determine when the spot 27 had reached equal dimness in sequential tests, the subject cannot falsify his/her acuity by consciously looking away from the spot, while achieving comparable acuity scores in the several tests.

The present invention may slso be employed to measure the phoria of the subject. For this procedure, a pair of polarizing filters, each 90° out of phase with the other, are fitted to respective lenses 14. The lamp power supply 66 is actuated by the control logic to provide constant voltage to the projector 26, which is also fitted with a polarizing filter or slide. The eye tracking sensors are aligned and actuated as before, but the waveform generator and ramp signal generator remain deactuated.

Due to the crossed polarized filters and the polarized spot, the subject sees the spot clearly with one eye, and not at all with the other eye. If the unseeing eye diverges from the seeing eye, the eye movement signal for the former will diverge from the latter. These signals are compared by the differential amplifier, and the arithmetic difference signal thereof is conducted through line 76 to the converter 77. This converter is a similar linear or non-linear device such as a resistance network or amplifier which has a response function equal to the functional relationship between phoria and the difference signal voltage. This signal is fed through line 78 to the display device 69. The control logic switches the device 69 to the phoria display mode, and the phoria of the subject is displayed in the proper units.

Thus it may be seen that the present invention provides a novel device for measuring visual acuity, both under normal conditions or following medical or visual stress, and phoria which is quick, easy to use, accurate, and foolproof.

We claim:

1. A device for measuring visual acuity both under normal conditions as well as following medical or visual stress comprising
    means for projecting a moving spot of light in the view of a subject,
    means for attenuating the intensity of said spot of light,
    eye tracking means for sensing the position of the eyes of the subject while said spot of light is present,
    difference means for comparing the position of the eyes of the subject and the position of said spot of light, including detector means for sensing divergence therebetween,
    converter means for converting said intensity of said spot of light at the instance of said divergence, to visual acuity units, and
    display means for displaying the output of said converter means.

2. The device of claim 1, wherein said eye tracking means comprises a plurality of infrared sensors producing a voltage analog signal corresponding to the position of the eyes of the subject.

3. The device of claim 1, wherein said spot of light moves in correspondence with a low frequency alternating current signal, and said difference means comprises a differential amplifier for comparing said voltage analog signal and said low frequency alternating current signal.

4. The device of claim 1, wherein said first means includes a projector directed at a mirror, said mirror moving in oscillating fashion.

5. The device of claim 4, wherein said mirror is secured to the armature of a galvanometer.

6. The device of claim 5, wherein said galvanometer is actuated by a low frequency alternating current signal.

7. The device of claim 4, wherein said second means includes a controlled amplitude power supply connected to said projector.

8. The device of claim 7, further including a ramp voltage signal generator controlling said power supply, said ramp voltage signal generator producing a smoothly decreasing voltage signal, and said power supply delivering a corresponding decreasing voltage to said projector.

9. The device of claim 8, wherein said converter means includes a voltage converter connected to said ramp voltage signal generator to convert said ramp voltage signal to a corresponding visual acuity signal.

* * * * *